(12) United States Patent
Chen et al.

(10) Patent No.: US 11,497,748 B2
(45) Date of Patent: Nov. 15, 2022

(54) METHOD FOR ACTIVATING AMPK AND THE USE OF ADENINE

(71) Applicant: Energenesis Biomedical Co., Ltd., Taipei (TW)

(72) Inventors: Han-Min Chen, Taipei (TW); Cheng-Yi Kuo, Taipei (TW); Chun-Fang Huang, Taipei (TW); Jiun-Tsai Lin, Taipei (TW)

(73) Assignee: Energenesis Biomedical Co., Ltd., Taipei (TW)

( * ) Notice: Subject to any disclaimer, the term of this patent is extended or adjusted under 35 U.S.C. 154(b) by 0 days.

(21) Appl. No.: 16/419,884

(22) Filed: May 22, 2019

(65) Prior Publication Data

US 2019/0269688 A1    Sep. 5, 2019

Related U.S. Application Data

(62) Division of application No. 13/859,741, filed on Apr. 10, 2013, now Pat. No. 10,335,412.

(51) Int. Cl.
*A61K 31/52* (2006.01)

(52) U.S. Cl.
CPC .................................. *A61K 31/52* (2013.01)

(58) Field of Classification Search
CPC ...................................................... A61K 31/51
See application file for complete search history.

(56) References Cited

U.S. PATENT DOCUMENTS

| | | | |
|---|---|---|---|
| 5,547,942 A | 8/1996 | Rapaport | |
| 5,840,705 A | 11/1998 | Tsukada et al. | |
| 1,135,468 A * | 2/1999 | Tomoko et al. | |
| 6,312,663 B1 | 11/2001 | Boykin, Jr. | |
| 6,342,484 B1 | 1/2002 | Kulkarni et al. | |
| 6,379,666 B1 | 4/2002 | Tobinick | |
| 10,335,412 B2 | 7/2019 | Chen et al. | |
| 10,500,206 B2 * | 12/2019 | Chen | A61K 31/52 |
| 2007/0021342 A1 | 1/2007 | Breen et al. | |
| 2007/0254853 A1 * | 11/2007 | Van Buren | A61K 31/7076 514/44 R |
| 2008/0228456 A1 * | 9/2008 | Clermont | G06F 19/00 703/11 |
| 2009/0131537 A1 | 5/2009 | Wille, Jr. | |
| 2010/0009927 A1 * | 1/2010 | Alberte | A61K 31/19 514/35 |
| 2011/0213020 A1 * | 9/2011 | Escaich Ferrer | A61K 36/06 514/44 R |
| 2011/0288106 A1 | 11/2011 | MUeller et al. | |
| 2018/0256585 A1 | 9/2018 | Chen et al. | |
| 2019/0269689 A1 | 9/2019 | Chen et al. | |
| 2019/0269690 A1 | 9/2019 | Chen et al. | |
| 2020/0093829 A1 | 3/2020 | Chen et al. | |

FOREIGN PATENT DOCUMENTS

| | | |
|---|---|---|
| CN | 105879006 A | 8/2016 |
| EP | 2342978 A2 | 7/2011 |
| WO | 1995/01097 A1 | 1/1995 |
| WO | 1999/37151 A1 | 7/1999 |

OTHER PUBLICATIONS

JP-1135468A Machine English Translation.*
U.S. Appl. No. 13/859,741, filed Apr. 10, 2013, Granted.
U.S. Appl. No. 16/419,892, filed May 22, 2019, Pending.
U.S. Appl. No. 16/419,927, filed May 22, 2019, Pending.
U.S. Appl. No. 15/456,815, filed May 13, 2017, Published.
Kedar, Can We Prevent Parkinson's and Alzheimer's Disease? JPGM, 49(3):236-245 (2003).
Skoog et al., Phytochemistry, 1967, vol. 6, pp. 1169-1192.
U.S. Appl. No. 16/419,884, filed Feb. 22, 2019, Method for activating AMPK and the use of Adenine.
Vingtdeux et al. The FASB Journal, vol. 25, No. 1, pp. 219-231, Jan. 2011.
Wroblewska 2012, Acta Agrobotanica, vol. 65(4), pp. 101-108.
Young et al., Investigation of the effects and molecular mechanism of adenine for diabetic wound healing. EASD Virtual Meeting, 1 page, ePoster #970, Sep. 13, 2016.
Patten et al., Reactive oxygen species: stuck in the middle of neurodegeneration. J Alzheimers Dis. 2010;20 Suppl 2:S357-67.
Watanabe et al., Neuroprotective effect of adenine on purkinje cell survival in rat cerebellar primary cultures. J Neurosci Res. Dec. 1, 2003;74(5):754-9.

* cited by examiner

*Primary Examiner* — Kara R Mcmillian
(74) *Attorney, Agent, or Firm* — McCarter & English, LLP; Yu Lu

(57) ABSTRACT

The present invention relates to adenine which is useful to activate AMP-activated protein kinase (AMPK) and the use of adenine in the prevention or treatment of conditions or disease and thereby prevent or treat conditions or diseases which can be ameliorated by AMPK in a mammal.

2 Claims, No Drawings

METHOD FOR ACTIVATING AMPK AND THE USE OF ADENINE

REFERENCE TO RELATED APPLICATIONS

This application is a divisional application of U.S. patent application Ser. No. 13/859,741, filed on Apr. 10, 2013, now allowed. The entire content of the above-referenced application is incorporated by reference herein.

BACKGROUND OF THE INVENTION

1. Technical Field

The present invention relates to adenine which is useful to activate AMP-activated protein kinase (AMPK) and the use of adenine in the prevention or treatment of conditions or disease.

2. Description of Related Art

Adenosine 5'-monophosphate-activated protein kinase (AMPK) is a cellular energy sensor and a responder to energy demand. AMPK is a heterotrimer composed of catalytic α subunit and regulatory β, γ subunits. All these subunits are highly conserved in eukaryotes. The activation of AMPK is through phosphorylation on the conserved $172^{th}$-threonine residue of a subunit by upstream kinases such as LKB1, $Ca^{2+}$/Calmodulin dependent kinase, and TAK1. High AMP/ATP ratio caused by physiological or pathological stress activates AMPK. Upon activation, AMPK activates catabolic pathway and inhibits anabolism which in term restores cellular energy balance by decreasing ATP consumption and promoting ATP generation.

As a regulator of energy homeostasis, AMPK has been suggested to be a potential drug target for metabolic syndromes including type II diabetes, cardio-vascular disease, and fatty liver disease. Many of the metabolic syndromes are linked to insulin resistance. Insulin resistance is a pathological condition in which cells fail to respond to insulin thus excess glucose in the blood stream cannot be removed into skeletal muscle or fat tissue. The activation of AMPK increases protein level of GLUT4, a glucose transporter, via transcriptional regulation and induces GLUT4 translocation to the plasma membrane in muscle cells in an insulin independent manner resulting in increases in the rate of cellular glucose uptake. Activation of AMPK also inhibits fatty acids and cholesterol synthesis via suppressing acetyl-CoA carboxylase and HMG-CoA reductase, respectively. In addition, activation of AMPK leads to inhibition of several transcription factors, including SREBP-1c, ChREBP and HNF-4a, and down-regulates the expression of enzymes which are mainly involved in fatty acid synthesis and gluconeogenesis. These findings support the idea that AMPK is a target of choice in the treatment of metabolic syndrome, in particular, diabetes.

In addition to the regulation of energy homeostasis, AMPK has been implicated in modulating several cellular mechanisms including inflammation, cell growth, apoptosis, autophagy, senescense and differentiation. Extensive studies demonstrate AMPK is a repressor of inflammation. Activation of AMPK can inhibit inflammation via suppressing NF-κB signaling. NF-κB signaling is the principle pathway that activates innate and adaptive immunity. The activation of AMPK can inhibits NF-κB transcriptional activity indirectly via stimulating SIRT1, Forkhead box O (FoxO) family or peroxisome proliferator-activated receptor co-activator 1α (PGC1α). Several groups also demonstrate that activation of AMPK suppresses protein expression of cyclooxygenase-2 (COX-2). COX-2 is an inducible enzyme which controlled by pro-inflammatory cytokines and growth factors. COX-2 converts arachidonic acid into prostaglandin which results in inflammation and pain. Inhibition of COX-2 activity or expression has been linked to anti-inflammation.

Several AMPK activators have been demonstrated to possess anti-inflammatory function in vivo. For example, 5-aminoimidazole-4-carboxamide ribonucleoside (AICAR) has been shown to ameliorate acute and relapsing colitis mouse model induced by 2,4,6-trinitrobenzene sulfonic acid (TNBS) or dextran sulfate sodium. AICAR treated mice showed reduced body weight loss and significant attenuation of inflammation. AICAR also showed therapeutic effects in treating experimental autoimmune encephalomyelitis (EAE), an animal model of multiple sclerosis and decreases severity of LPS-induced lung injury in mice.

Dysregulation of cellular signaling pathway can lead to abnormal cell growth and ultimately, cancer. The mammalian target of rapamycin (mTOR) is a serine/threonine kinase which regulates cell proliferation and autophagy. The activity of mTOR signaling pathway is dys-regulated in many different cancers and therefore mTOR inhibitors are considered as potential drugs for cancer therapy. There are extensive studies demonstrate that AMPK phosphorylates tuberous sclerosis complex 2 (TSC2) and Raptor to inhibit mTOR pathway. A variety of AMPK activators including AICAR, metformin, phenformin has also been demonstrated suppressed mTOR signaling and inhibited cancer cell growth. In addition, activation of AMPK induces autophagy via suppressing mTORC1 activity. Due to the inhibition of mTORC1 by AMPK, phosphorylation of Ulk1 on $Ser^{757}$ is decreased and subsequently Ulk1 can be phosphorylated by AMPK on $Ser^{317}$ and $Ser^{777}$. The AMPK-phosphorylated Ulk1 is active and then initiates autophagy.

Base on above mentioned, AMPK has been suggested as a good target in many human diseases or pathological conditions including inflammatory disease, wound healing, neurodegeneration, cancer, oxidative stress and cardiovascular disease. In fact, AMPK activators have been applied for clinical trials in at least 24 disease categories including bacterial and fungal diseases, behaviors and mental disorders, blood and lymph conditions, cancers and other Neoplasms, digestive system diseases, diseases and abnormalities at or before birth, ear, Nose, and throat diseases, eye diseases, gland and hormone related diseases, heart and blood diseases, immune system diseases, mouth and tooth diseases, muscle, bone, and cartilage diseases, nervous system diseases, nutritional and metabolic diseases, occupational diseases, parasitic diseases, respiratory tract (lung and bronchial) diseases, skin and connective tissue diseases, substance related disorders, symptoms and general pathology, urinary tract, sexual organs, and pregnancy conditions, viral diseases, wounds and injuries. Herein we disclosed a novel AMPK activator, adenine and the use of this compound in the prevention or treatment of diseases.

BRIEF SUMMARY OF THE INVENTION

According to one embodiment of the present invention there is provided a novel AMPK activator, adenine, for activating AMPK in cells and thereby prevent or treat conditions or diseases which can be ameliorated by AMPK in a mammal.

According to one embodiment of the present invention there is provided a method for reducing blood glucose via activating AMPK in a cell and thereby prevent or treat diseases including metabolic syndrome, type 2 diabetes, insulin resistance wherein an effective amount of adenine and/or the pharmaceutically acceptable salts thereof, is administered to a mammal in need of such treatment.

According to one embodiment of the present invention there is provided a method for anti-inflammation via activating AMPK in a cell and thereby treat inflammatory condition or disease, wherein an effective amount of adenine and/or the pharmaceutically acceptable salts thereof, is administered to a mammal in need of such treatment.

According to one embodiment of the present invention there is provided a method for reducing Aβ accumulation via activating AMPK in a cell and thereby prevent or treat Alzheimer's disease, wherein an effective amount of adenine and/or the pharmaceutically acceptable salts thereof, is administered to a mammal in need of such treatment.

According to one embodiment of the present invention there is provided a method for suppressing fibroblast proliferation via activating AMPK and thereby prevent scar formation during wound healing.

According to one embodiment of the present invention there is provided a method to enhance wound healing, wherein an effective amount of adenine and/or the pharmaceutically acceptable salts thereof, is administered to a mammal in need of such treatment.

According to one embodiment of the present invention there is provided a method to inhibit ROS production in a cell and thereby protect or treat cells from ROS injury in mammal, wherein an effective amount of adenine and/or the pharmaceutically acceptable salts thereof, is administered to a mammal in need of such treatment.

According to one embodiment of the present invention there is provided a method to inhibit cancer cells proliferation and thereby prevent or treat cancer, wherein an effective amount of adenine and/or the pharmaceutically acceptable salts thereof, is administered to a mammal in need of such treatment.

Thus, the present invention relates to adenine which is useful to activate AMP-activated protein kinase (AMPK) and the use of adenine in the prevention or treatment of diseases, including pre-diabetes, insulin resistance, type 2 diabetes, metabolic syndrome, obesity, inflammation, wound healing, Alzheimer's disease, cancer, oxidative stress and cardiovascular disease.

BRIEF DESCRIPTION OF THE DRAWINGS

No Drawing

DETAILED DESCRIPTION OF THE INVENTION

The inventors have unexpectedly discovered that adenine is a novel AMPK activator and has various biological functions in mammals. In recent years, the activation of AMPK has been shown to be beneficial in the prevention and the treatment of diseases such as pre-diabetes, insulin resistance, type 2 diabetes, metabolic syndrome, obesity, inflammation, Alzheimer's disease, cancer, oxidative stress and cardiovascular disease as well as enhancing wound healing. The inventors contemplate that such effects can be attributed to the activation of AMPK which result in but not limited to the reduction of COX-2, ROS production and increase of glucose uptake.

As used herein, the term "AMPK" refers to adenosine 5'-monophosphate-activated protein kinase. The term "AMPK activator" used herein refers to a compound which can enhance or stabilize phosphorylation of $172^{th}$-threonine residue of subunit of AMPK and hence activates AMPK activity.

Contemplated Indications

Base on the inventor's findings (see examples below), it's contemplated that adenine can be used as a therapeutic agent for various conditions or diseases via activating AMPK. The following provides exemplary guidance and evidence on contemplated indications.

Adenine in the Treatment of Hyperglycemia, Pre-Diabetes, Insulin Resistance, and Type 2 Diabetes It has recently been reported that AMPK activators including metformin, A769662, AICAR reduced plasma glucose in diabetic or obesity mice models. In the present invention, 1 μM~600 μM of adenine significantly increased glucose uptake of C2C12 muscle cells (Table 2). To further evaluate the effects of adenine on the modulation of plasma glucose level, the high-fat diet-fed mice were served as a type 2 diabetes animal model. Chronic treatment of high-fat diet-fed mice with adenine significantly reduced plasma glucose by more than 30% and decreased plasma triacylglycerides by more than 35% compared to the control mice. A more-than-15% decrease in body weight was also observed (example 3).

As used herein, "hyperglycemia" refers to physiological condition characterized by blood sugar higher than 126 mg/dL. "pre-diabetes" refers to a physiological condition characterized by a fasting blood sugar higher than 100 mg/dL but below than 140 mg/dL. "Insulin resistance" used herein refers to a physiological condition in which whole body or tissues including liver, skeletal muscle, adipose tissue fail to response to insulin. "type 2 diabetes" used herein also known as noninsulin-dependent diabetes mellitus (NIDDM) or adult-onset diabetes. It refers to a metabolic disorder caused by insufficient insulin production or insulin resistance which often manifested by a fasting glucose higher than 140 mg/dL. According to the examples, adenine was found to accelerate glucose uptake, therefore was suggested as a useful treatment to the conditions or diseases which associated with high blood glucose.

Adenine in the Treatment of Inflammation

Various AMPK activators have been demonstrated possess anti-inflammatory function in vivo. For example, daily treatment of 5-aminoimidazole-4-carboxamide ribonucleoside (AICAR) in 2,4,6-trinitrobenzene sulfonic acid (TNBS) or dextran sulfate sodium-treated mice ameliorates acute and relapsing colitis by reduced body weight loss and significant attenuation inflammation. Treatment of AICAR had therapeutic effects in experimental autoimmune encephalomyelitis (EAE), an animal model of multiple sclerosis. Treatment of AICAR to mice decreased severity of LPS-induced lung injury. In the present invention, adenine inhibited LPS-induced inflammation in vitro: under LPS stimulation, the secretion level of pro-inflammatory cytokines including TNFα, IL-1β and IL-6 were significantly reduced in adenine treated macrophages compared to control cells. Adenine also decreased COX-2 expression which was induced by LPS in human macrophages (example 4). In TNBS-induced inflammatory bowel disease (IBD) mice model chronic treatment with adenine significantly reduced pro-inflammatory cytokines including TNF, INFγ and IL-17 in colon compare to control mice and rescued body weight loss in these mice (example 5).

As used herein, "pro-inflammatory cytokines" refers to cytokines which promote systemic inflammation. "Inflammatory diseases" used herein refers to diseases associate with inflammation including but not limited to ankylosing spondylitis, arthritis (osteoarthritis, rheumatoid arthritis (RA), psoriatic arthritis), asthma, atherosclerosis, Crohn's disease, colitis, dermatitis, diverticulitis, fibromyalgia, hepatitis, irritable bowel syndrome (IBS), systemic lupus erythematous (SLE), nephritis, Alzheimer's, Parkinson's disease and ulcerative colitis. "COX-2" used herein refers to cyclooxygenase 2 which converts arachidonic acid into prostaglandin. Recently, several reports demonstrate that AMPK is an upstream regulator of COX-2 and suppresses COX-2 protein expression. The same with previous findings, we found that a novel AMPK activator, adenine can also suppress COX-2 expression which suggest adenine may be a useful compound to inhibit COX-2 mediated inflammation. According to the present invention, adenine was found to be able to inhibit inflammation, therefore was suggested as a useful treatment to the conditions or diseases which associated with inflammation.

Adenine in wound healing and scar formation AMPK has been suggested to promote cell motility and enhance wound healing in cultured cells. An AMPK activator, resveratrol, has been found to enhance incisional wound healing. In addition to closing the wound, reducing scar formation during the healing process has been a preferred goal in modern medicine. Neonatal wound healing, unlike adult wound healing, does not accompany scar formation. The difference is in Cox-2 activation. In adult wound healing, COX-2 activity will be elevated (by TGF-beta), resulting in the increased production of prostaglandin at wound sites. Prostaglandin promotes fibroblast growth and collagen formation, two factors that lead to scar formation. Hence, inhibition of COX-2 activities has been considered as effective treatment in preventing scar formation. In the present invention, adenine inhibited human fibroblast cell growth (example 8) and reduce COX-2 expression. Using animal model, topical treatment of adenine at wound site enhanced not only wound closure but also reduced scar formation (example 9). According to above data, topical administration of adenine is useful to enhance would healing and prevent scar formation.

Neurodegeneration

Defects in several different cellular mechanisms has been linked to neurodegeneration, including inflammation, intracellular trafficking, and autophagy. Autophagy functions to remove dysfunctional organelles or protein aggregates in the cell and play a crucial part in maintaining cellular homeostasis. Pathogenesis of many neurodegenerative diseases involves the presence of intracellular or extracellular protein aggregate deposits. Removal of these protein aggregates has been shown to ameliorate the progression of these diseases. Impaired autophagy pathway or removal of proteins responsible for autophagy has been linked to neurodegeneration.

AMPK activation has been shown to facilitate autophagy pathway. Therefore, promotion of autophagy pathways via activation of AMPK may be a useful strategy to prevent or control neurodegeneration. AMPK activators have been shown to decrease amyloid deposition via autophagy pathway. Daily resveratrol administration increases life span in AD mice models. Another AMPK activator, curcumin, has also been demonstrated as a potential drug for AD therapy. In the present invention, we found that adenine significantly enhanced autophagy activity and reduced Aβ accumulation in a dose-dependent manner in Neuro2A cells and improved cognitive function in AD mice model (example 6 and 7). According to these findings, adenine can be useful in the treatment of neurodegenerative diseases.

As used herein, "neurodegeneration" refers to the condition which is progressive loss of structure or function of neurons. Neurodegenerative disease is a result of neurodegenerative processes including Alzheimer's disease (AD), Parkinson's disease (PD), Huntington's disease (HD), amyotrophic lateral sclerosis (ALS), Spinocerebellar ataxia (SCA), Spinal muscular atrophy (SMA), etc.

ROS Associated Diseases

Reactive oxygen species (ROS) including superoxide radicals, hydroxyl redical and hydrogen peroxide are continuously produced in tissues. A variety of diseases have been associated with excessive ROS including NARP (neurogenic muscle weakness, ataxia and retinitis pigmentosa), MELAS (mitochondrial encephalomyopathy, lactic acidosis, and stroke-like episodes), MERRF (myoclonic epilepsy and ragged-red fibers), LHON (Leber hereditary optic neuropathy), and KSS (Kearns-Sayre syndrome, ophthalmoplegia, ataxia, retinitis pigmentosa, cardiac conduction defect and elevated cerebrospinal fluid protein), Parkinson disease (PD), Alzheimer's disease (AD), amyotrophic lateral sclerosis (ALS), Huntington's disease (HD), and Friedreich's ataxia (FA) and aging. Numerous reports demonstrate that AMPK activator, AICAR, reduced ROS production under high-glucose, palmitate or albumin induction. In the present invention, adenine was found to reduce ROS production in a dose-dependent manner in HUVEC cell (Table 4), therefore was suggested as a useful treatment to the conditions or diseases which associated with ROS.

Cancer

Activation of AMPK suppressed COX-2 and mTOR pathways which are important mechanisms of cancer cells growth. Due to the contribution of mTOR and COX-2 to cancer aggressiveness, activation of AMPK is suggested as a rational strategy for cancer therapy. Indeed numerous reports have demonstrated that AMPK activators interrupt cancer progression. For example, biguanide AMPK activators (phenformin and metformin) have been found to inhibit breast tumor development and growth in xenografts mice models. In the present invention, adenine was found to inhibit proliferation of human hepatocellular carcinoma cell line Hep G2, human breast adenocarcinoma cell line MCF7 and human colon adenocarcinoma grade II cell line HT29 (example 11). The IC50 of adenine for HepG2, MCF7 and HT29 were 544.1, 537.5 and 531.9 μM, respectively. In HepG2 transplanted mice, chronic treatment with adenine significantly delayed tumor growth in dose-dependent manner. According to present invention, the treatment with adenine to activate AMPK activity may prevent or control cancer development and progression.

Example 1

AMPK Activation Assay

Effects of adenine on AMPK activation were evaluated based on the phosphorylation of AMPK protein upon adenine treatment. Mouse muscle cell C2C12, mouse fibroblast 3T3, human liver carcinoma cell Hep G2, human umbilical vein endothelial cell HUVEC, Human acute monocytic leukemiacell THP1, human macrophage cell U937, murine microglia cell BV-2, and mouse neuroblastoma cell Neuro2A were cultured in high-glucose Dulbecco's modified Eagle's medium (DMEM) containing 10% fetal bovine serum (FBS), 4 mM L-glutamine, 2 mM sodium pyruvate and 1% penicillin/streptomycin (Invitrogen GibcoBRL, Carlsbad, Calif., USA) at 37° C. under 5% $CO_2$. Cells were plated at $3\times10^5$ per well in 6-well plates. 24 h after plating, adenine was added to the culture media as indicated. After 30 min cells were lysed and subject to western blot analysis. Equal amount of protein from each sample was separated by SDS-PAGE and then electroblotted on to PVDF membranes. Membranes were blocked with 3% BSA in PBS for 60 min and incubated with an anti-phospho-AMPK (Thr172) antibody (1:2,000, Cell signaling) or an anti-AMPK antibody (1:2,000, Cell signaling) at 4° C. overnight followed by the corresponding secondary antibody for 1 h at room temperature (RT). Immunoreactive bands were detected by enhanced chemiluminescence (ECL; Pierce, Rockford, Ill., USA) and recorded using Kodak film (Rochester, N.Y., USA). The detected signals were scanned and then quantified using TotalLab Quant software (TotalLab).

The effect of adenine on AMPK activation is summarized in Table 1. Adenine significantly activated AMPK in all tested cells including C2C12, 3T3, Hep G2, MCF7, HT29, THP1, HUVEC, U937, BV2, Dermal Papilla and Neuro2A cells.

TABLE 1

| Cells | Concentration of adenine (microM) | AMPK activation (fold to control) |
|---|---|---|
| C2C12 | 1 | 1.2 |
|  | 10 | 1.7 |
|  | 100 | 3.2 |
|  | 200 | 3.9 |
|  | 600 | 4.1 |
| 3T3 | 1 | 1.1 |
|  | 10 | 1.5 |
|  | 100 | 2.9 |
|  | 200 | 4.0 |
|  | 600 | 4.2 |
| Hep G2 | 1 | 1.1 |
|  | 10 | 2.1 |
|  | 100 | 3.3 |
|  | 200 | 3.8 |
|  | 600 | 4.2 |
| MCF7 | 1 | 1.2 |
|  | 10 | 1.6 |
|  | 100 | 2.5 |
|  | 200 | 3.4 |
|  | 600 | 3.7 |
| HT29 | 1 | 1.1 |
|  | 10 | 1.7 |
|  | 100 | 2.9 |
|  | 200 | 3.4 |
|  | 600 | 3.8 |
| HUVEC | 1 | 1.2 |
|  | 10 | 1.9 |
|  | 100 | 3.2 |
|  | 200 | 3.9 |
|  | 600 | 4.1 |
| THP1 | 1 | 1.2 |
|  | 10 | 2.2 |
|  | 100 | 3.7 |
|  | 200 | 4.3 |
|  | 600 | 4.2 |
| U937 | 1 | 1.1 |
|  | 10 | 1.3 |

TABLE 1-continued

| Cells | Concentration of adenine (microM) | AMPK activation (fold to control) |
|---|---|---|
|  | 100 | 2.9 |
|  | 200 | 3.7 |
|  | 600 | 4.0 |
| BV-2 | 1 | 1.2 |
|  | 10 | 1.7 |
|  | 40 | 2.6 |
|  | 160 | 3.2 |
| Neuro2A | 1 | 1.2 |
|  | 10 | 2.1 |
|  | 100 | 3.4 |
| Dermal Papilla | 1 | 1.1 |
|  | 10 | 1.4 |
|  | 100 | 2.1 |
|  | 200 | 2.5 |
|  | 600 | 2.8 |

Example 2

Glucose Uptake In Vitro

Effects of adenine on glucose uptake were analyzed by measuring the uptake of fluorescent glucose analog (2-NBDG, Molecular Probes) in muscle cell C2C12. C2C12 were treated with indicated concentrations of adenine for 30 min at 37° C. then incubated with 500 μM of fluorescent glucose analog. After 5 min incubation at room temperature, cells were washed three times with Kreb-Hepes buffered solution and fixed in 70% alcohol. The fluorescence of glucose analog in cells was measured using a Fluorescence Microplate Reader System at 480-nm excitation and 530-nm emission wavelength.

The effect of adenine on glucose uptake is summarized in Table 2. Adenine significantly stimulated glucose uptake in C2C12 cells in dose-dependent manner. Data are presented as the mean±SEM of three independent experiments.

TABLE 2

| Agent | Concentration (microM) | Glucose uptake (% to control) |
|---|---|---|
| Adenine | 1 | 117 ± 8.1 |
|  | 10 | 261 ± 13.4 |
|  | 100 | 315 ± 11.9 |
|  | 600 | 338 ± 16.5 |

Example 3

Anti-Diabetic Effects of Adenine

To further evaluate the effects of adenine on the modulation of plasma glucose level, the high-fat diet-fed mice were served as a type 2 diabetes animal model. C57BL/6J mice were maintained at 22° C. under a 12-h light/dark cycle and fed either a high fat diet (60% kcal % fat) or a normal diet ad libitum. Intraperitoneal injections of adenine (0.1 to 50 mg/kg) or vehicle were given to the high-fat diet-fed mice from the age of 24 weeks and glucose readings were measure at 1 and 3 hr. IP administration of adenine or vehicle only to the high-fat diet-fed mice continued twice a day for 6 days. On day 6, plasma was collected 1 hr after the last dosing for analyzing, evaluating, measuring plasma glucose and triglycerides. Adenine-injected group showed >30% lower plasma glucose and more than 35% lower plasma triacylglycerides as well as more than 15% lower body weight compare to the control group.

Example 4

Adenine Suppressed Inflammatory Response Induced by LPS In Vitro

Effects of adenine on inflammatory response were evaluated in human THP1 macrophage by examining protein level of intracellular COX-2 and secreted TNFα, IL-1β and IL-6. Differentiation of THP1 monocytes into macrophages was induced by 50 nM PMA for 24 hr. THP1 macrophages were further stimulated by 50 ng LPS for 6 hr in the presence of 10-600 μM of adenine or vehicle followed by cell lysis and western blot analysis. Equal amounts of protein were separated by SDS-PAGE and then electroblotted on to PVDF membranes. Membranes were blocked with 3% BSA in PBS for 60 min and incubated with an anti-COX-2 antibody (1:1,000, Cell signaling), an anti-actin antibody (1:5,000, Cell signaling) at 4° C. overnight followed by the corresponding secondary antibody for 1 h at room temperature (RT). Immunoreactive bands were detected by enhanced chemiluminescence (ECL; Pierce, Rockford, Ill., USA) and recorded using Kodak film (Rochester, N.Y., USA). The detected signals were scanned and then quantified using TotalLab Quant software (TotalLab). The secreted TNFα, IL-1β and IL-6 were analyzed by enzyme-linked immunosorbent assays. The expression of COX-2 and secretion level of TNFα, IL-1β and IL-6 were significantly reduced in adenine treated macrophages compared with control cells.

TABLE 3

| Adenine (microM) | TNF . (% to control) | IL-1β. (% to control) | IL-6 (% to control) | COX-2 (% to control) |
|---|---|---|---|---|
| 0 | 100 ± 4.7 | 100 ± 11.3 | 100 ± 8.5 | 100 ± 2.9 |
| 10 | 85 ± 9.1 | 91 ± 8.4 | 88 ± 6.3 | 81 ± 4.4 |
| 100 | 41 ± 2.6 | 29 ± 5.5 | 21 ± 7.8 | 59 ± 3.5 |
| 600 | 23 ± 1.8 | 17 ± 3.7 | 14 ± 6.2 | 38 ± 5.3 |

Example 5

Adenine Suppressed 2,4,6-Trinitrobenzene Sulfonic Acid (TNBS) Induced Inflammation In Vivo To further evaluate the effects of adenine on inflammatory response, TNBS-induced inflammatory bowel disease (IBD) mice model was used. C57BL/6J mice were maintained at 22° C. under a 12-h light/dark cycle. Relapsing colitis was induced with five escalating doses of TNBS, 0.5 mg, 0.75 mg, 1.0 mg, 1.25 mg, and 1.5 mg, in 50% ethanol were administered respectively for 0.1 mL per mouse weekly. Control mice were given 0.1 mL of saline alone by intrarectal administration. After the third administration of TNBS, daily intraperitoneal injection of adenine (0.01, 0.1, 5 or 30 mg/kg body weight) or vehicle were given to mice. Two days after the last TNBS administration, mice were sacrificed. The inflammatory cytokines including TNF, INFγ and IL-17 from colonic lysates were evaluated by enzyme-linked immunosorbent assays. The level of TNF, INFγ and IL-17 were significantly reduced in colon of adenine treated mice in dose-dependent manner compared with non-adenine treated mice. In addition, treatment of adenine also rescued the body weight loss caused by TNBS.

Example 6

Amyloid β Peptide and Autophagy Assay

Effects of adenine on Amyloid β peptide were analyzed in mouse neuroblastoma cell Neuro2A. Neuro2A cells were cultured in high-glucose Dulbecco's modified Eagle's medium (DMEM) containing 10% fetal bovine serum (FBS), 4 mM L-glutamine, 2 mM sodium pyruvate and 1% penicillin/streptomycin (Invitrogen GibcoBRL, Carlsbad, Calif., USA) at 37° C. under 5% $CO_2$. Cells were plated at $3 \times 10^5$ per well (6-well plate). 24 h after plating, cells were transfected with human APP695 and treated with indicated concentration of adenine for 24 h followed by cell lysis and western blot analysis. Equal amounts of protein were separated by SDS-PAGE and then electroblotted on to PVDF membranes. Membranes were blocked with 3% BSA in PBS for 60 min and incubated with an anti-Aβ antibody (1:1,000, abcam), an anti-LC3 antibody (1:1,000, Cell signaling), and an anti-actin antibody (1:5,000, Cell signaling) at 4° C. overnight followed by the corresponding secondary antibody for 1 h at room temperature (RT). Immunoreactive bands were detected by enhanced chemiluminescence (ECL; Pierce, Rockford, Ill., USA) and recorded using Kodakfilm (Rochester, N.Y., USA). The detected signals were scanned and then quantified by using TotalLab Quant software (TotalLab).

The effects of adenine on sAβ production and LC3-II/LC3-I ratio are summarized in Table 4. Adenine significantly reduced Aβ amount and increased LC3-II/LC3-I ratio in dose-dependent manner in Neuro2A cells. Because the conversion of LC3-I to LC3-II is indicative of autophagy activity, the higher LC3-II/LC3-I ratio in adenine treated cells reflects the ability of adenine to induce autophagy activity.

TABLE 4

| Adenine (microM) | sAβ level (% of control) | LC3-II/LC3-Iratio (relative to control) |
|---|---|---|
| 0 | 100 ± 6.1 | 1.0 ± 0.1 |
| 10 | 89 ± 7.5 | 1.2 ± 0.1 |
| 20 | 63 ± 2.2 | 1.8 ± 0.3 |
| 30 | 48.1 ± 1.7 | 2.8 ± 0.2 |
| 40 | 31.7 ± 5.1 | 2.9 ± 0.2 |
| 50 | 29.4 ± 3.6 | 3.2 ± 0.3 |

Example 7

Adenine Rescued Neurodegeneration of Aβ-Induced Alzheimer's Disease Model Mice

Aβ25-35 was purchased from Sigma-Aldrich (St. Louis, Mo.). The peptides were dissolved in distilled saline and aggregated by incubation at 37° C. for 7 days before injection. C57BL/6J mice were maintained at 22° C. under a 12-h light/dark cycle. Adult mice were anesthetized by ketamine (500 mg/kg) and xylazine (100 mg/kg) and placed in a stereotaxic frame (Stoelting, Wood Dale, Ill., USA). 5 nmol of the aggregated Aβ25-35 were injected into the lateral ventricle using a 10-μl Hamilton syringe (Hamilton Company, Reno, Nev., USA). The target anterior-posterior (AP), medial-lateral (ML) and dorsoventral coordinates were −0.5 mm, ±1 mm and −2.5 mm relative to the bregma. To evaluate the effect of adenine on neurodegenerative disease, Aβ infusion mice were daily intraperitoneally injected with 0.01, 0.1, 5 or 30 mg/kg bodyweight of adenine or vehicle for 4 weeks. The cognitive functions of these mice were analyzed by using Morris water maze assay after 4 weeks injection. The water maze was performed in a circular pool filled with water and a platform was submerged below the water's surface in the target quadrant for hidden platform test. During the 5-day hidden platform test, mice were randomly placed into starting points of the pool in each daily trial (6 trials per day). The probe trial was performed 1 day after 5-day hidden platform test. For the probe trial, the platform used in the hidden platform test was removed and the starting point was in the quadrant opposite the target quadrant. Mice were allowed to swim in the maze for 60 s and recorded by a video camera. The latency to find the platform and swim paths were analyzed by EthoVision software (Version 3.1, Noldus, The Netherlands). In the hidden platform test, adenine treated AD mice took significantly shorter time to find platform in dose-dependent manner than control AD mice. This result demonstrated adenine treatment rescued the impairments of special learning and memory of AD mice. Further, adenine treated AD mice spent higher percentage time in target quadrant in probe assay than control AD mice, which indicated that adenine improve the retention of memory.

Example 8

Adenine Inhibited Fibroblast Proliferation

Human fibro blast cell line 3T3 were cultured in high-glucose Dulbecco's modified Eagle's medium (DMEM) containing 10% fetal bovine serum (FBS), 4 mM L-glutamine, 2 mM sodium pyruvate and 1% penicillin/streptomycin (Invitrogen GibcoBRL, Carlsbad, Calif., USA) at 37° C. under 5% $CO_2$. For cell proliferation assay, 3T3 cells were plated at $1×10^5$ per well (6-well plate). 24 h after plating, cells were treated with indicated concentration of adenine for 72 h and the number of viable cells was counted. Cells were detached using trypsin-EDTA solution and stained with trypan blue. The living cells were counted using hemocytometer. The effects of adenine on 3T3 cell proliferation are summarized in Table 5. Adenine significantly inhibited 3T3 cell proliferation in dose-dependent manner. Data are presented as the mean±SEM of three independent experiments.

TABLE 5

| Adenine (microM) | Cell number (% to control) |
|---|---|
| 0 | 100 ± 4.3 |
| 10 | 91 ± 2.7 |
| 50 | 73 ± 8.1 |
| 100 | 64 ± 5.3 |
| 200 | 48 ± 2.8 |
| 500 | 33 ± 6.4 |
| 1000 | 27 ± 11.3 |

Example 9

Adenine Enhances Wound Healing and Reduces Scar Formation

C57BL/6J mice were maintained at 22° C. under a 12-h light/dark cycle. The experiments were performed with 12-weeks old mice. After anesthetized by an intraperitoneal injection of ketamine (500 mg/kg) and xylazine (100 mg/kg), 6-mm full-thickness excisional skin wounds was made on the backs of mice using 6-mm skin biopsy punches. Immediately after wounding, 10-1200 M of adenine in 25 l saline or saline alone was applied to the wound bed. The skin wounds were then covered by semipermeable transparent dressing and fixed to the skin. The mice were treated with adenine or vehicle for 14 days and then sacrificed. The scar formation is assessed by Masson's trichrome staining to observe the fibrosis process and the collagen framework of the healed wound (Fixed by 4% paraformaldehyde). After 14 days of treatment, the extent of closure was significantly greater in adenine treated mice in dose-dependent manner than in control mice. According to histological examination of the regenerated tissue, topical treatment with adenine significantly decreased the scar width 14 days post-wounding compared to vehicle treated wounds.

Example 10

Adenine Reduced ROS Production

HUVECs were cultured in Dulbecco's modified Eagle's medium (DMEM) containing 10% fetal bovine serum (FBS), 4 mM L-glutamine, 2 mM sodium pyruvate and 1% penicillin/streptomycin (Invitrogen GibcoBRL, Carlsbad, Calif., USA) at 37° C. under 5% $CO_2$. Cells were plated at $2×10^4$ per well in black 96-well. 24 h after plating, medium was changed to fresh DMEM containing either 5.6 or 30 mM glucose and treated with indicated concentration of adenine or vehicle. 24 hr after treatment, the intracellular ROS was detected using $H_2$DCF-DA. Cells were washed once with PBS and then incubated with 100 μM DCF at 37° C. for 30 min then the fluorescence of DCF was measured using a Fluorescence Microplate Reader System at 485-nm excitation and 530-nm emission wavelengths.

The effect of adenine on ROS production is summarized in Table 4. Adenine significantly reduced hyperglycemia-induced ROS production in dose-dependent manner in HUVECs.

TABLE 4

| Adenine (microM) | Glucose (mM) | ROS production (% of 5.6 mM glucose) |
|---|---|---|
| 0 | 30 | 275 ± 8.1 |
| 10 | 30 | 211 ± 4.3 |
| 100 | 30 | 116 ± 1.7 |
| 200 | 30 | 38.1 ± 2.9 |
| 600 | 30 | 21.7 ± 3.1 |
| 1200 | 30 | 22.4 ± 2.5 |

Example 11

Cancer Cell Growth Inhibition Assay

Human liver hepatocellular carcinoma cell line Hep G2, human breast adenocarcinoma cell line MCF7 and human colon adenocarcinoma grade II cell line HT29 were used to evaluate the effects of adenine on cell proliferation. Those cell lines were obtained from ATCC and were cultured in high-glucose Dulbecco's modified Eagle's medium (DMEM) containing 10% fetal bovine serum (FBS), 4 mM L-glutamine, 2 mM sodium pyruvate and 1% penicillin/streptomycin (Invitrogen GibcoBRL, Carlsbad, Calif., USA)

at 37° C. under 5% $CO_2$. Cells were plated at $1\times10^5$ per well (6-well plate). 24 h after plating, cells were treated with indicated concentration of adenine for 48 h and then followed by cell counting. Cells were detached using trypsin-EDTA solution and stained with trypan blue. The living cells were counted using hemocytometer. The IC50 of adenine for HepG2, MCF7 and HT29 were 544.1, 537.5 and 531.9 µM, respectively.

Example 12

Tumor Growth Assay

Human liver hepatocellular carcinoma cell line Hep G2 were cultured in high-glucose Dulbecco's modified Eagle's medium (DMEM) containing 10% fetal bovine serum (FBS), 4 mM L-glutamine, 2 mM sodium pyruvate and 1% penicillin/streptomycin (Invitrogen GibcoBRL, Carlsbad, Calif., USA) at 37° C. under 5% $CO_2$. For tumor implantation, $5\times10^6$ Hep G2 cells were injected subcutaneously into 8-week-old male nonobese diabetic-severe combined immunodeficiency (NOD-SCID) mice. After implantation, the mice were daily intraperitoneally injected with 5, 20 or 50 mg/kg body weight of adenine or vehicle and the tumor size was monitored every 3 days. The growth of tumor was significantly retarded in adenine treated mice compared with control mice 14 days post implantation.

It should be apparent, however, to those skilled in the art that many more modifications besides those already described are possible without departing from inventive concepts herein. The embodiments are not intended to limit the scope of the present invention. The scope of the present invention is defined only by the appended claims.

The invention claimed is:

1. A method for treating asthma, comprising administrating to a mammal in need thereof with an effective amount of adenine and/or a pharmaceutically acceptable salt thereof as a sole active ingredient, wherein the asthma is a subtype of asthma caused by a COX-2 mediated inflammation.

2. A method for treating an inflammatory condition or disease, comprising administrating to a mammal in need thereof with an effective amount of adenine and/or a pharmaceutically acceptable salt thereof as a sole active ingredient, wherein the inflammatory condition or disease is one subtype caused by a COX-2 mediated inflammation and selected from the group consisting of ankylosing spondylitis, arthritis, asthma, atherosclerosis, fibromyalgia, and systemic lupus erythematous.

* * * * *